United States Patent [19]

Bartoo et al.

[11] Patent Number: 4,743,248
[45] Date of Patent: May 10, 1988

[54] DOSAGE FORM FOR DELIVERING ACID SENSITIVE BENEFICIAL AGENT

[75] Inventors: Marc L. Bartoo, Seattle, Wash.; Patrick S. L. Wong, Hayward; Felix Theeuwes, Los Altos, Calif.; Brian Barclay, Sunnyvale, Calif.

[73] Assignee: ALZA Corporation, Palo Alto, Calif.

[21] Appl. No.: 895,551

[22] Filed: Aug. 11, 1986

[51] Int. Cl.$^4$ ............................................... A61K 9/22
[52] U.S. Cl. .......................... 604/892.1; 604/890.1; 424/472
[58] Field of Search .............. 604/890–892, 604/896; 424/19–21, 451, 455, 456, 457, 458, 459, 464, 465, 468, 472, 473, 474, 475, 482

[56] References Cited

U.S. PATENT DOCUMENTS

| | | | |
|---|---|---|---|
| 3,916,899 | 11/1975 | Theeuwes et al. | 128/260 |
| 4,200,098 | 4/1980 | Ayer et al. | 128/260 |
| 4,285,987 | 8/1981 | Ayer et al. | 128/260 |
| 4,503,030 | 3/1985 | Edgren et al. | 424/473 |
| 4,578,075 | 3/1986 | Urquhart et al. | 604/892 |
| 4,584,188 | 4/1986 | Graham | 424/19 |
| 4,615,698 | 10/1986 | Guittard et al. | 424/19 |
| 4,624,848 | 11/1986 | Lee | 424/19 |
| 4,627,850 | 12/1986 | Deters et al. | 604/890 |

OTHER PUBLICATIONS

Lappas et al., *Polymeric Pharmaceutical Coating Materials I-Preparation and Properties*, Feb. 1965, Journal of Pharmaceutical Sciences, vol. 54, No. 2, pp. 176–181.

Lappas et al., *Polymeric Pharmaceutical Coating Materials II-In Vivo Evaluation as Enteric Coatings*, Oct. 1967, Journal of Pharmaceutical Sciences, vol. 56, No. 10, pp. 1257–1261.

Primary Examiner—C. Fred Rosenbaum
Assistant Examiner—Sharon E. Rose
Attorney, Agent, or Firm—Paul L. Sabatine; Edward L. Mandell; Shelley G. Precivale

[57] ABSTRACT

A dosage form is disclosed, which dosage form comprises an outside wall and an inside wall, which inside wall comprises means for changing its structural integrity in response to fluid having a pH greater than 5 that enters the dosage form, thereby changing the pH environment inside the dosage form and concomitantly causing the inside wall to change its structural integrity, thus causing the outside wall to collapse and be easily eliminated from a host.

10 Claims, 2 Drawing Sheets

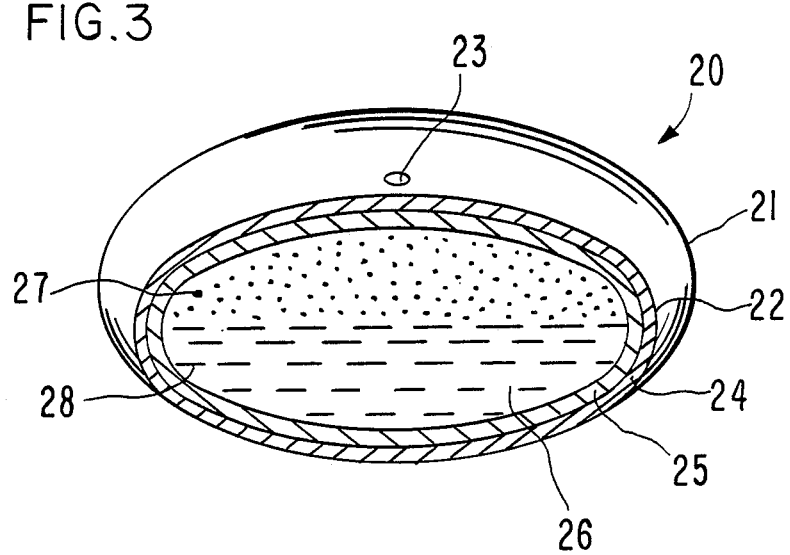
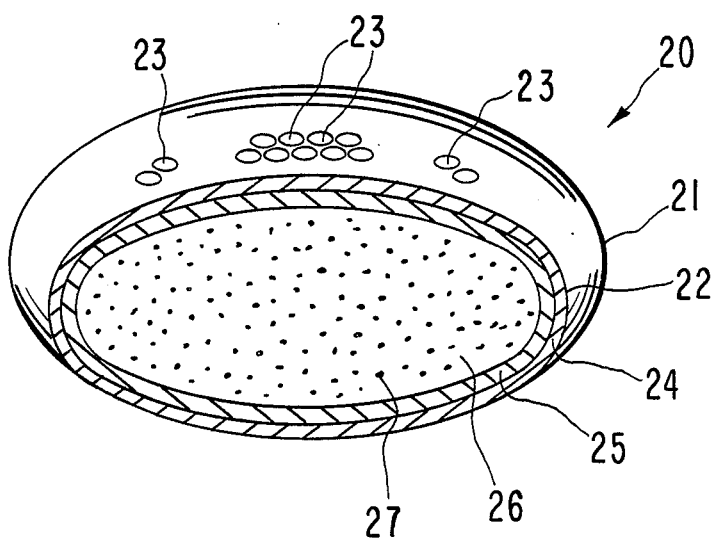

DOSAGE FORM FOR DELIVERING ACID SENSITIVE BENEFICIAL AGENT

FIELD OF THE INVENTION

This invention pertains to both a novel and unique dosage form. The dosage form comprises an inner wall, an outer wall and a compartment comprising a beneficial agent that exhibits in solution a pH less than 7. In operation the beneficial agent is continuously delivered from the dosage form and at the end of the delivery period alkaline solution present in the environment of use enters the dosage form changes and alters the structural integrity of the inner wall, whereupon the dosage form collapses thereby facilitating discharge of the dosage form from the environment of use.

BACKGROUND OF THE INVENTION

Since the beginning of antiquity, both pharmacy and medicine have sought a dosage form for the controlled administration of a beneficial drug. The first written reference to a dosage form is in the Eber Papyrus written about 1552 B.C. The Eber Papyrus mentioned dosage forms such as anal suppositories, vaginal pessaries, ointments, oral pill formulations and other dosage preparations. About 2500 years passed without any advance in dosage form development until the Arab physician Rhazes, 863-925 A.D., invented the coated pill. About a century later the Persian Avicenna, 980-1037 A.D., coated pills with gold or silver for increasing patient acceptability and for enhancing the effectiveness of the drug. Also, around this time, the first tablet was described in Arabian manuscripts written by Al-Zahrawi, 936-1009 A.D. The manuscripts described a tablet formed from the hollow impressions in two matched-facing tablet molds. Pharmacy and medicine waited about 800 years for the next innovation in dosage forms when in 1833 Mothes invented the soft gelatin capsule for administering a drug. Fifteen years later, in 1848 Murdock invented the two-piece hard gelatin capsule. The coating of pills with tolu was first recommended about 1860, and in 1884 Unna introduced enteric coating with Keratin coated pills.

The technical valve of sustained released dosage forms was recognized by Lipowski who, in 1938, discussed the desirability of a slow and constant supply of a drug to an organism. Lipowski's patents were the first to describe an oral dosage for consisting of a number of small drug containing beads, having different thickness of coating, utilized to give a slow and constant release of drug on ingestion. In 1952 Blythe conceived of the use of multiple small pellets which could be coated and which, independent of pH, would have reproducible release rates and prolonged drug release. Blythe uses varying coating thicknesses of time-delay materials in a single capsule.

The next quantum and profound advancement in dosage forms came in 1972 with the invention of the osmotic delivery system by inventors Theeuwes and Higuchi. This unique osmotic dosage form is manufactured in one embodiment for oral use, and in this embodiment it embraces the appearance of a tablet with at least one delivery portal. The delivery portal can be preformed or formed by leaching a pore former during operation of the dosage form. It is the first oral dosage form that delivers throughout the entire gastrointestinal tract a known amount of drug per unit time at a controlled rate of delivery. The oral osmotic device maintains its physical and chemical integrity during the prolonged period of time it transits the total length of the gastrointestinal tract.

The above discussed osmotic dosage form represents an outstanding and pioneering advancement in the art and science of drug delivery. Now it has been discovered a need exists for a delivery system that loses its physical and chemical integrity at the end of the delivery period for discharging the dosage form from the environment of use, mainly the gastrointestinal tract. The need exists for a dosage form that loses its structural integrity, that is for a dosage form that becomes compressible and/or self-destructs for avoiding possible retention of the empty dosage form within the gastrointestinal tract.

OBJECTS OF THE INVENTION

Accordingly, in view of the above presentations, it is an immediate object of this invention to provide a novel and useful dosage form that satisfies that critical need associated with the prior art.

Another object of the invention is to provide a novel dosage form that delivers substantially all of its beneficial agent from the dosage from followed by the dosage form collapsing for easy passage from the gastrointestinal tract.

Another object of the present invention is to provide a dosage form manufactured as an osmotic device shaped, sized, structured and adapted for the controlled and continuous delivery of a beneficial drug throughout the gastrointestinal tract followed by the device losing its structural integrity at the end of the delivery period for facilitating easy exit from the tract.

Another object of the present invention is to provide a controlled time release dosage form comprising an inner wall that breaks down at the end of the delivery period for enhancing the peristaltic expulsion of the dosage form from the environment of use.

Another object of the present invention is to provide a dosage that delivers a drug constantly for sustained blood levels in the body as a result of controlled and sustained release of drug in the gastrointestinal tract, comprising the stomach and the intestines, and which dosage form under the influence of the alkaline environment of the intestine alters and changes its structure for enhancing its peristaltic expulsion from the intestine.

Another object of the present invention is to provide an oral, osmotic dosage form for delivering essentially all of its drug at a controlled rate in the stomach and in the intestines, with the dosage form keeping its physical and chemical integrity during the drug dispensing in the stomach and intestine and then losing its physical and chemical integrity after the dispensing period in the intestine, and which dosage form is relatively economical in cost to manufacture, provides the physician with a dependable dosage form, and is well-adapted for practical and acceptable patient use.

Another object of the present invention is to provide an oral, osmotic device that dispenses drug at a rate controlled by the device in the stomach and in the intestine and then in response to the biological environment of the intestine adapts a structure that is readily discharged from the animal body.

Other objects features and advantages of this invention will be more apparent to those versed in the dispensing art from the following detailed specification, taken in conjunction with the drawings and the accompanying claims.

BRIEF DESCRIPTION OF THE DRAWINGS

In the drawing figures, which are not drawn to scale but are set forth to illustrate various embodiments of the present invention, the drawing figures are as follows:

FIG. 4 is a view of another embodiment of the dosage form of FIG. 1 seen in opened section for illustrating a different releasing means of the dosage form.

In the drawing figures, and in the specification, like parts in related figures are identified by like numbers. The terms appearing earlier in the specification, and in the description of the drawing figures, as well as embodiments thereof, are further described elsewhere in the disclosure.

DETAILED DESCRIPTION OF THE DRAWING FIGURES

Figure 1:
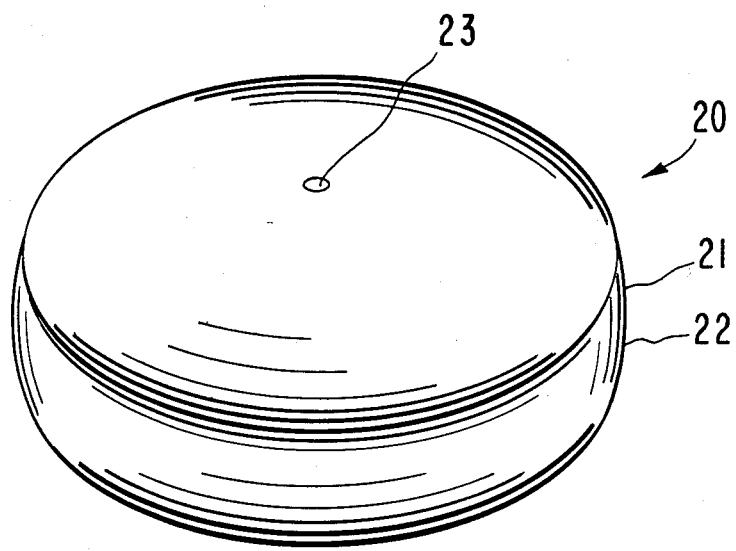
FIG. 1 is a general view of a dosage form manufactured as an osmotic device for dispensing a beneficial agent throughout the gastrointestinal tract.

Turning now to the drawing figures in detail, which drawing figures are an example of the dosage form provided by this invention, and which examples are not to be construed as limiting the invention, one example of the dosage form is illustrated in FIG. 1 and designated by the numeral 20. In FIG. 1, dosage form 20 comprises a body member 21 comprising a wall 22 that surrounds and forms an internal compartment not seen in FIG. 1. Dosage form 20 further comprises at least one exit means 23 for connecting the interior of dosage form 20 with the exterior environment of use.

Figure 2:
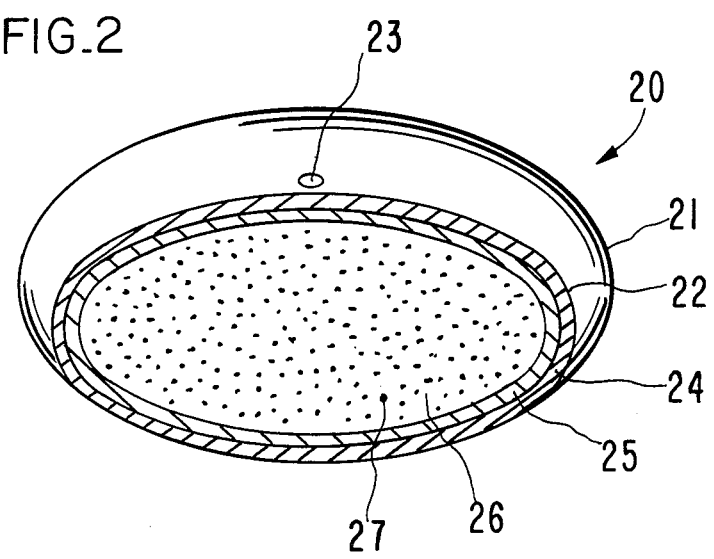
FIG. 2 is a view of the dosage form of FIG. 1 seen in opened view for illustrating the internal structure of the dosage form; and, FIG. 3 is a view of another embodiment of the dosage form of FIG. 1 seen in opened section for illustrating a different internal structure of the dosage form.

FIG. 2 illustrates dosage form 20 of FIG. 1 comprising body 21, wall 22, and exit means 23. Wall 22 comprises an outer wall 24 and an inner wall 25. Wall 22 comprising outside wall 24 and inside wall 25 surrounds and defines an interior compartment 26. Composite wall 22, comprising outside wall 24 and inside wall 25 at least in part, or totally, comprises a composition that is permeable to the passage of an exterior fluid present in the environment of use. Outside wall 24 comprises a polymeric composition that is inert and maintains its physical and chemical integrity during the dispensing life time of dosage form 20. The phrase "physical and chemical integrity" denotes outside wall 24 does not lose its structure and it does not change during the dispensing life of dosage form 20. Typical materials for forming outside wall 24 comprises selectively semipermeable polymers known as osmosis and as reverse osmosis polymers. These polymeric compositions comprise a cellulose ester, cellulose ether, cellulose ester-ether, cellulose acylate, cellulose diacylate, cellulose triacylate, cellulose acetate, cellulose diacetate, and cellulose triacetate. Other semipermeable polymeric compositions include cellulose acetate ethyl carbamate, cellulose acetate methyl carbamate, cellulose acetate ethyl carbamate, cellulose acetate succinate, cellulose acetate dimethyl-aminoacetate, cellulose acetate ethyl-carbamate, cellulose acetate chloracetate, cellulose dipalmate, cellulose dioctanoate, cellulose acetate valerate, cellulose acetate succinate, cellulose propionate succinate, and the like. In a presently preferred embodiment outside wall 24 comprises a thickness of from 0.01 mm to 3 mm. Semipermeable polymers are known to the dispensing art in U.S. Pat. Nos. 3,845,770; 3,916,899; 4,160,020 and 4,250,108.

Inside wall 25 comprises a polymeric formulation that is sensitive to changes in pH. Wall 25 keeps its physical and chemical integrity in the presence of beneficial acidic agents that form an acidic solution having a pH less than 4 with fluid that enters dosage form 20. Inside wall 25 maintains its integrity throughout the dispensing of the beneficial agent from dosage form 20. Inside wall 25, in a preferred embodiment, loses its integrity when a solution having a pH greater than 5 present in the environment of use enters the dosage form and causes inside wall 25 to lose its integrity. The loss of integrity of inside wall 25 is accompanied by a collapse of outside wall 24 thereby increasing its discharge from the environment of use. Representative materials for forming inside wall 25 are materials that dissolve or disintegrate on exposure to the alkaline solution or the alkaline environment inside dosage form 20. The solution also includes the intestinal buffer solution of the gastrointestinal tract. The materials for forming inside wall 25 include ionizable polyacids, frequently a long-chain polymer with ionizable carboxyl groups and the like. Materials for forming inside wall 25 include keratin, keratin over sandarac-tolu, B-naphthyl benzoate and acetotanin, balsam of Peru, balsam of tolu, shellac, gum resin and salol-shellac formalized gelatin, myristic acid-hydrogenated castor oil, shellac n-butyl stearate, cellulose carboxylic acid phthalate, cellulose ethyl phthalate, cellulose acetate phthalate, starch acetate phthalate, amylose acetate phthalate, hydroxypropyl methylcellulose phthalate, hydroxypropyl ethylcellulose phthalate, cellulose acetate hexahydrophthalate, hydroxypropyl methylcellulose hexahydrophthatate, polyacylic acid, polyacylic acid co-esters, and the like. Inside wall 25 is preferably from 1 mm to 5 mm thick. In in vitro test for determining the disintegration rate and time of a material in an alkaline environment is reported in *Pharmaceutical Technology,* by Chambliss, Sept. 1983. Materials sensitive to pH are reported in *Remington's Pharmaceutical Sciences.* 14th Ed., pp 604 to 605, 1965; and in Biopharmaceutics and Relevant Pharmacokinetics, 1st Ed., pp 158 to 165, 1971.

Internal compartment 26 comprises a beneficial agent 27, that is in a presently preferred embodiment a beneficial drug. The drug that can be housed in compartment 26 includes any physiologically or pharmacologically active drug that produces a local or a systemic effect in animals. The term animals includes warm-blooded mammals, humans, primates, household, sport, farm and zoo animals. The active drugs that can be delivered include inorganic and organic drugs without limitations, drugs that can act on the central nervous system, depressants, hypnotics, sedatives, psychic energizers, tranquilizers, anticonvulsants, muscle relaxants, antiparkinson, anti-inflammatories, local anesthetics, muscle contractants, antimicrobials, antimalarials, hormonal agents, contraceptives, diuretics, sympathomimetics, antiparasitics, neoplastics, hypoglycemics, ophthalmics, diagnostics, cardiovascular drugs and the like. The beneficial drugs useful for the purpose of the present invention comprises drugs, or a drug and an acidic osmagent, or a drug and an acidic buffer, that exhibit an acidic pH in solution. The beneficial drugs are in a presently preferred embodiment the acid addition drugs. Examples of non-toxic, pharmaceutically acceptable acid addition salts are hydrochloric, hydrobromic, sulfuric, phosphoric, acetic, propionic, citric, oxalic, maleic, and the like. More specific examples of acid drugs that exhibit a pH of less than 4 comprise a member selected from the group consisting of cyclizine hydrochloride, thiethylperazine maleate, diphenoxyleate hydrobromide, phentolamine mesylate, cyclopentolate hydrochloride, mepenzolate bromide, cyclomethycaine sulfate, tripelennamine citrate, trimeprazine tartrate, and the like. The beneficial drugs are known to the art in *Pharmaceutical Sciences*, by Remington, 14th Ed., 1979 published by Mack Publishing Co., Easton, Pa.; *The Drug, The Nurse, The Patient*, Including current Drug Handbook, 1974–76, by Falconer et al., published by Saunders Co., Philadelphia, Pa.; and *Physician's Desk Reference*, 40th Ed., 1986, published by Medical Economics Co., Oradell, N.J.

The term "pH" as used herein denotes the pH valve of an aqueous solution as a number describing its acidity or alkalinity. The pH valves are determined by acid-base titrations, and by using electronic pH meters as reported in the *Encyclopedia Of Chemistry*, 2nd Ed., pages 799 to 800, 1966, published by Van Nostrand-Reinhold Co., New York, N.Y. The effects of an acidic solution, or a alkaline solution on the integrity of a pH sensitive materials in direct contact with the solution is ascertainable by the procedures described in *J. Amer. Pharm. Assoc.* Vol. 27, pp 379 to 384, 1938; and *The Pharmacopeia Of The United States Of America*, 18th Ed., pp 932 to 934, 1970.

FIG. 3 is a opened view of another dispensing dosage form 20 provided by this invention. In FIG. 3, dosage form 20 comprises body 21, and dual wall 22. Dual wall 22 comprises outside wall 24 that permits the passage of fluid into dosage form 20 and inside wall 25 formed of an alkaline-sensitive material. Inside wall 25 loses its integrity after the dispensing of drug from dosage form 20 and in the presence of biological alkaline fluid from the intestine and the colon that enters dosage form 20 after the dispensing of the drug. Dual wall 22 surrounds interior compartment 26 comprising at least one exit means 23.

Internal compartment 26 of FIG. 3, in a presently preferred embodiment, houses a first layer 27 comprising a beneficial drug identified by dots, and an expandable layer 28, identified by dashes. Drug formulation 27 was described above in the presentation pertaining to FIG. 2. Expandable layer 28 comprises a hydrophilic, hydrogel formulation that exhibits fluid absorbing and-/or imbibing properties. The hydrophilic materials forming layer 28 comprises a hydrophilic polymeric formulation that can interact with water and aqueous biological fluids and swell or expand to an equilibrium state. In operation, first layer 27 and second layer 28 cooperate to deliver drug formulation from dosage 20, with second layer absorbant fluid expanding and exerting pressure against first layer 27. First layer 27 optionally absorbs fluid and forms a dispensable formulation and by the combined operations second layer 28 expands against first layer 27 and urge it from compartment 26. In this manner, drug formulation is delivered through exit means 23 to the environment of use.

The hydrophilic hydrogel composition comprising layer 28 swells or expands to a very high degree, usually exhibiting from a nonhydrated state, a 2 to 50 fold increase in volume. Representative hydrophillic hydrogels consists of a member selected from the group consisting of poly(hydroxyalkyl methacrylate) having a molecular weight of 15,000 to 5,000,000; poly(vinylpyrrolidone) having a molecular weight of about 10,000 to 360,000; poly(vinyl alcohol) having a low acetate content and lightly cross-linked with glyoxal, formaldehyde or glutaraldehyde and having a degree of polymerization of from 200 to 30,000; poly(ethylene oxide) having a molecular weight from 10,000 to 6,000,000; the sodium salt of carboxymethylcellulose having a molecular weight from 10,000 to 2,000,000; acidic carboxy polymer known as carboxypolymethylene and carboxyvinyl polymers consisting of acrylic acid lightly cross-linked with polyallyl sucrose and sold under the trademark Carbopol ®, acidic carboxypolymer having a molecular weight of 200,000 to 6,000,000, including sodium acidic carboxyvinyl hydrogel and potassium acidic carboxyvinyl hydrogel; Cyanamer ® polyacrylamide; and the like. The representative polymers are known in the *Handbook Of Common Polymers*, by Scott and Roff, published by the Chemical Company, Cleveland, Ohio; *ACS Symposium Series*, No. 31, by Ratner and Hoffman, pp 1 to 36, 1976, published by the American Chemical Society; and in *Recent Advances In Drug Delivery Systems* by Schacht, pp 259 to 278, published by Plenum Press, N.Y.

FIG. 4 depicts in opened section another delivery dosage form 20 provided by the invention. Dosage form 20 in FIG. 4 comprise.s body member 21, wall 22 comprising outside wall 24 and inside 25, compartment 26 comprising drug formulation 27 and exit means 23. The expression exit means as used herein comprises means and methods suitable for releasing drug formulation 27 from compartment 26. The expression "at least one passageway" includes aperture, orifice, bore, pore, porous element through which drug can migrate, a hollow fiber, capillary tube and the like. The expression includes also a material that erodes, or is leached from wall 22 in the fluid environment of use to produce at least one passageway in the dosage form. Representative materials suitable for forming at least one passageway, or a multiplicity of passageways include an erodible poly(lactic) or poly(glycolic) acid member in the wall, a gelatinous filament, leachable materials such a fluid removable pore forming polysaccharides, salts, oxides or salt alcohols, and the like. A passageway or plurality of passageways can be formed through the outside and inside walls by leaching a material such as sorbitol from the walls to produce a controlled release passageway. Dosage form 20 can be constructed with one or more passageways in spaced apart relation on more than one surface of a dosage form. The passageway can be a microporous member inserted into the wall, with the microporous member preformed or formed during operation of the dosage form. Passageways and equipment for forming passageways are disclosed in U.S. Pat. Nos. 3,916,899; 4,063,064 and 4,088,864. Passageways of controlled dimensions in an osmotic system formed by leaching a pore former such as sorbitol are disclosed in U.S. Pat. No. 4,200,098.

The amount of drug present in the dosage form generally is an amount sufficient for performing a therapeutic program. Generally, the dispensing dosage form will contain from 0.05 ng to 1500 mg, or more with individual dosage forms containing, for example, 25 ng, 1 mg, 25 mg, 50 mg, 125 mg, 250 mg, 750 mg, and the like. The dosage form can be administered once, twice daily, or like, over a prolonged period of one day to one year, or longer. The phrase drug formulation as used for the purpose of this invention denotes the drug is present in the compartment neat, or with tablet forming excipients.

Wall 22, comprising outside wall 24 and inside wall 25, surrounding drug formulation 27, or surrounding drug formulation 27 and expandable member 28, in the various embodiments can be formed using an air suspension procedure. The procedure consists in suspending and tumbling the compartment forming members and wall forming compositions in a current of air and using the wall forming composition until the inside wall, and then the outside wall is applied to the compartment forming members. The air suspension procedure is well-suited for independently forming each wall in separate operations. The air suspension procedure is described in U.S. Pat. No. 2,799,240; in *J. Am. Pharm. Assoc.*, Vol. 48, pp 451 to 459, 1959; and ibid, Vol. 49, pp 82 to 84, 1960. The wall-forming composition can be applied with a Wurster ® air suspension coater, or an Aeromatic ® air suspension coater. Other wall-forming techniques such as pan coating can be used for providing the dosage form. In the pan coating system, the wall forming compositions are deposited by successive spraying of the composition accompanied by tumbling in a rotating pan. A pan coater is used to produce a thicker wall. Finally, the wall coated dosage form is dried in a forced air oven at 50° C. for a week, or in a temperature and humidity controlled oven, at 50° C. and 50° C. R.H. for 24 hours.

Exemplary solvents operable for manufacturing a wall of a dosage form include inert organic and inorganic solvents that do not adversely harm the wall forming material, and the final dosage form. The solvents broadly include a member selected from the group consisting of an alcohol, ketone, ester, ether, aliphatic, halogenated, cycloaliphatic, aromatic, heterocyclic, aqueous solvents, and the like.

The compartment forming members comprising a drug and other ingredients are manufactured in one process by blending a powdered drug and other core forming ingredients in a fluid bed granulator. After the powdered ingredients are dry blended in the granulator, a granulating fluid, for example, polyvinyl pyrrolidone in water, is sprayed onto the powdered member. The coated powder is dried in the granulator. After drying a lubricant such as magnesium stearate is added to the granulator. The granules are then pressed and wall coated with a wall forming composition.

The dosage form of the invention can be manufactured by other manufacturing techniques. For example, in one manufacture the beneficial drug and other compartment core forming materials are blended and pressed into a solid layer. The layer possesses dimensions that corresponds to the internal dimensions of the area occupied in the dosage form. Optionally, the drug formulation can be blended with a solvent, mixed by conventional methods such as ballmilling, callendering, stirring, or rollmilling and then pressed into a preselected shape. The compressed compartment forming mass then is coated with an inner and outer wall. The wall forming composition can be applied by press coating, molding, spraying, dipping or air suspension procedures. The air suspension and air tumbling procedures comprise suspending and tumbling the pressed composition until surrounded with the respective walls. Dosage forms comprising a drug formulation layer in contacting arrangement, and then coated with the inner and outer walls.

In another manufacture, the dosage form is made by the wet granulation technique. In the wet granulation technique, the drug is blended with other compartment forming ingredients using an organic cosolvent, such as isopropyl alcohol-methylene dichloride, 80/20 v/v (volume/volume) as the granulation fluid. The ingredients are passed through a 40 mesh screen and blended in a mixer. Then, the blend is dried for 18 to 24 hours at 42° C. in a forced air oven. Next, a lubricant is added to the dry blend, and the newly formed mixture put into milling jars and mixed on a jar mill for 5 to 15 minutes. The composition is pressed into a layer in a Manesty ® layer press at a maximum load of 2 tons. The pressed mass is fed to a Kilian ® dry cota press and coated with an exterior wall.

DESCRIPTION OF EXAMPLES OF THE INVENTION

The following examples are merely illustrative of the present invention and they should not be considered as limiting the scope of the invention in anyway, as these examples and other equivalents thereof will become more apparent to those versed in the dispensing art in the light of the present disclosure, the drawing figures and the accompanying claims.

EXAMPLE 1

A dosage form is manufactured for delivering a beneficial drug as follows: first, a compartment-forming composition is prepared by dissolving 4 g of polyvinyl pyrrolidone in 30 ml of a cosolvent consisting of 95% ethanol and 5% distilled water, and then blending the moist polyvinyl pyrrolidone with a composition comprising 475 g of cimetidine hydrochloride and 10 g of cross-linked sodium carboxymethyl cellulose previously passed through a 40 mesh stainless steel sieve to yield a homogeneous blend. Next, an additional 70 ml of the cosolvent consisting of ethanol and distilled water is added to the cimetidine hydrochloric acid blend to form a wet granulation. The wet granulation is passed through a 10 mesh stainless steel sieve and then dried at 50° C. for 18 to 20 hours. Then 5 g of magnesium stearate is added to the dried granulation which is passed through a 20 mesh stainless steel sieve. The final blend is compressed into number of cores of drug having an average core weight of 742.2 mg and a hardness of 12-18 kp.

The individual cores were coated with an inside wall-forming composition comprising 30% hydroxypropylmethylcellulose phthalate, 15% cellulose acetate having an acetyl content of 39.8%, 45% sorbitol and 10% polyethylene glycol. The wall-forming coating solution consists of 80/20 (v/v) acetone/water blend. The total solid content is 3%, with mixing conducted with a Cole-Parmer ® stirrer. The wall forming composition is coated around the cores in an air suspension machine. The first applied inside wall is about 4 mils thick. Next, an outside wall about 0.5 mil thick comprising cellulose acetate having an acetyl content of 32% is applied in contacting arrangement over the first formed inside wall. The second form outside semipermeable wall is applied using a cosolvent comprising methylene chloride/methanol, 80/20, (v/v) with a total solid content of 2%. The wall forming semipermeable composition is mixed with a Cole-Parmer ® mixer and applied with an Aeromatic ® air suspension coater. The final dosage form has a pair of spaced apart passageways of 0.38 mm diameter. The dosage forms, after dispensing its drug in a distilled water environment is transferred to an artificial intestinal fluid environment. In the artificial intestinal fluid, the inside wall undergoes dissolution in the fluid, as the inside wall dissolves due to hydroxide ions from the artificial intestinal fluid entering the dosage form, thereby causing the dosage form to collapse.

EXAMPLE 2

The procedure described in Example 1 is repeated with all condition as previously set forth, except that in this example the outside semipermeable wall consists of cellulose acetate having an acetyl content of 36%, or cellulose acetate having an acetyl content of 39.8%. The initial collapse pressure of the cellulose acetate 36% wall, and the cellulose acetate 39.8% outside wall overcoated around the inside wall of Example 1 is 150 mm Hg, and 150 mm Hg respectively. The walls exhibited a collapse pressure of 60 mm Hg, are 60 mm Hg when exposed to artificial intestinal fluid, indicating the interior wall dissolves and weakens as to lose its structural integrity and continuity in the structural integrity and continuity in the presence of artificial intestinal fluid exhibiting a pH greater than 4. The dissolution of the wall in intestinal fluid enhances the easy of expulsion of the dosage form through the anorectal route from the gastrointestinal tract.

EXAMPLE 3

A dosage form for dispensing a beneficial drug having an acidic function is manufactured as follows: first, 600 g of indomethacin, 2220 g of polyethylene oxide having a molecular weight of 200,000 and 150 g of hydroxypropyl methyl cellulose are blended and screened 40 mesh screen and then added to a mixing bowl, and dry mixed for 15 to 20 minutes. Next, 2000 ml of anhydrous, denatured ethanol is slowly added and mixing continued for 15 to 20 minutes more. Then, the wet mass is passed through a 16 mesh screen, spread on a white paper overnight and air dried at room temperature. Next, the dry mass is passed through a 16-mesh screen and 30 g of magnesium stearate added and blended therewith for 5 minutes, to yield the drug containing core-forming composition.

Next, 4480 g of polyethylene oxide having a molecular weight of about 5,000,000 is screened through a 40 mesh screen. Then, 2030 g of sodium chloride, and 350 g of hydroxypropyl methylcellulose and mixed for 15 to 20 minutes. Next, a granulating solvent consisting of 6 L of ethanol absolute and 100 ml of methanol is slowly added to the blending ingredients and the wet granulation mixed for 5 to 10 minutes. The wet granulation is removed from the mixer and then passed through a 16 mesh screen onto paper-lined oven trays. The trays are placed into an oven at 30°–35° C. and allowed to dry for 24 hours. After drying the dry granulation is passed through a 16-mesh stainless steel screen and 30 g of magnesium stearate added thereto. Then, all the ingredients are blended for 15 minutes to provide a uniform, homogeneous hydrophilic, hydrogel composition.

Next, a number of drug cores weighing 60 mg are pressed into a layer and then placed into contacting arrangement with a 240 mg layer of the hydrophilic, hydrogel composition. The first and second layers are surrounded with a wall forming composition 22.5% hydroxypropylmethylcellulose phthalate, 25% hydroxypropylmethylcellulose, 25% polyethylene glycol, 22.5% cellulose acetate having an acetyl content of 39.8% and 5% of adipic acid. The wall is applied from a cosolvent comprising methylene chloride/methanol, 80/20 (v/v) with a total solid content of 4%. The wall forming ingredients were mixed with a Cole-Parmer ® stirrer and applied with an Aeromatic ® air suspension coater.

Then, a semipermeable wall is coated around the inside wall. The outside wall cellulose acetate having an acetyl content of 39.8%. The semipermeable wall is applied with a cosolvent comprising methylene chloride/methanol, 90/10, (v/v), with a solid content of 2%. The wall forming ingredients are mixed with a Cole-Parmer ® stirrer, and coated with an Aeromatic ® air suspension coater. The dosage form had a 0.38 mm orifice, and after dispensing its drug layer, the inside wall in artificial intestinal fluid exhibits fissuring and collapses for reducing the possible accumulation of dosage forms in the gastrointestinal tract.

EXAMPLE 4

The above procedure of Example 3 is repeated with all the conditions as set forth, except that in this example the outside wall comprises ethyl cellulose.

In summary, it will be readily appreciated that the present invention contributes to the art an unobvious dosage form manufactured as a drug delivery device possessing wide and practical application. While the invention has been described and pointed out in detail and with reference to operative embodiments thereof, it will be understood that those skilled in the art will appreciate that various changes, modifications, substitutions and omissions can be made without departing from the spirit of the invention. It is intended, therefore, that the invention embrace those equivalents within the scope of the claims which follow.

We claim:

1. A dosage form for dispensing a beneficial agent formulation to an environment of use, the dosage form comprising:
    (a) a first wall that permits the passage of fluid and comprises means for keeping its chemical integrity in a first fluid environment exhibiting a pH less than 5 and for losing its chemical integrity in a second fluid environment exhibiting a pH greater than 5;
    (b) a second wall that permits the passage of fluid and comprises means for keeping its chemical integrity in a first fluid environment exhibiting a pH less than 5 and for keeping its chemical integrity in a second environment exhibiting a pH greater than 5;
    (c) a compartment formed by the first wall and the second wall with the first wall surrounding and facing the inside of the compartment and the second wall surrounding the first wall and facing the environment of use;
    (d) a beneficial agent formulation in the compartment, which agent formulation forms with fluid that enters the compartment a fluid environment exhibiting a pH less than 5;
    (e) at lease one passageway through the walls for dispensing the beneficial agent formulation from the dosage form to the environment of use over time; and,
    (f) wherein, fluid from the environment exhibiting a pH greater than 5 enters the dosage form causing the first wall at the end of the dispensing of the beneficial agent to lose its chemical integrity for facilitating discharge of the dosage form from the environment of use.

2. The dosage form for dispensing the beneficial agent formulation according to claim 1, wherein the second wall contact the first wall.

3. The dosage form for dispensing the beneficial agent formulation according to claim 1, wherein the beneficial agent is a pharmaceutically acceptable acidic drug.

4. The dosage form for dispensing the beneficial agent formulation according to claim 1, wherein the beneficial agent is a drug comprising its pharmaceutically acceptable acid addition salt.

5. The dosage form for dispensing the beneficial agent formulation according to claim 1, wherein the first wall initially is thicker than the second wall.

6. A dosage form for dispensing a beneficial agent formulation to a biological environment of use, the dosage form comprising:
(a) a first wall that pemits the passage of fluid and comprises means for keeping its chemical integrity in a first fluid envirnoment inside the dosage form exhibiting a pH less than 5 and for losing its chemical integrity in a second fluid environment inside the dosage form exhibiting a pH greater than 5;
(b) a second wall that permits the passage of fluid and comprises means for keeping its chemical integrity in a first fluid environment exhibiting a pH less than 5 and for keeping its chemical integrity in a second environment exhibiting a pH greater than 5;
(c) a compartment formed by the first wall and by the second wall which first wall surrounds and faces the inside of the compartment and which second wall surrounds the first wall and faces the biological environment of use;
(d) a beneficial agent formulation in the compartment, which agent formulation forms with fluid that enters the compartment a fluid environment exhibiting a pH less than 5, and a hydrophilic hydrogel formulation in the compartment that aids in dispensing the agent formulation from the dosage form;
(e) at least one passageway through the walls connecting the compartment with the biological environment of use for dispensing the beneficial agent formulation from the dosage form over a prolonged period of time; and,
(f) wherein fluid from the environment having a pH greater than 5 enters the dosage form through the passageway causing the first wall at the end of the dispensing of the beneficial agent to lose its chemical interity for facilitating discharge of the dosage form from the environment of use.

7. The dosage form for dispensing the beneficial agen formulation according to claim 6, wherein the second wall contacts the first wall.

8. The dosage form for dispensing the beneficial agent formulation according to claim 6, wherein the beneficial agent is a pharmaceutically acceptable acidic drug.

9. The dosage form for dispensing the beneficial agent formulation according to claim 6, wherein the beneficial agent is a drug comprising its pharmaceutically acceptable acid addition salt.

10. The dosage form for dispensing the beneficial agent formulation according to claim 6, wherein the first wall initially is thicker than the second wall.

* * * * *